US006979688B2

(12) United States Patent
Ford

(10) Patent No.: US 6,979,688 B2
(45) Date of Patent: Dec. 27, 2005

(54) TREATMENT METHOD AGAINST SIDE-EFFECTS OF CHEMOTHERAPY

(76) Inventor: John P. Ford, 141 Main St., Box J, Unadilla, NY (US) 13849

( * ) Notice: Subject to any disclaimer, the term of this patent is extended or adjusted under 35 U.S.C. 154(b) by 0 days.

(21) Appl. No.: 10/684,203

(22) Filed: Oct. 10, 2003

(65) Prior Publication Data

US 2004/0077589 A1 Apr. 22, 2004

Related U.S. Application Data

(63) Continuation-in-part of application No. 10/364,383, filed on Feb. 12, 2003, now abandoned.
(60) Provisional application No. 60/355,764, filed on Feb. 12, 2002.

(51) Int. Cl.$^7$ ............................................. A61K 31/505
(52) U.S. Cl. ........................ 514/274; 514/690; 514/691
(58) Field of Search ................................ 514/274, 690, 514/691

(56) References Cited

PUBLICATIONS

Cao, S. et al., "5–Fluorouracil Prodrug: Role of Anabolic and Catabolic Pathway Modulation in Therapy of Colorectal Cancer", Clinical Cancer Research, vol. 1, pp. 839–845, Aug. 1995.*
Goodman & Gilman's The Pharmacological Basis of Therapeutics, 9$^{th}$ Edition, 1996, pp. 1225–1229.*
Stein, J. H., Editor–in–Chief, Internal Medicine, 4th Edition, Chapters 71 and 72, 1994.*
Chua D. et al., Proc Am Soc Clin Oncol 22. "Efficacy of capecitabine monotherapy in patients with recurrent and metastatic nasopharyngeal carcinoma pretreated with platinum–based chemotherapy," p. 511, 2003.
Childress J. et al., American Journal of Clinical Oncology, vol. 26, No. 5. "Cutaneous Hand and Foot Toxicity Associated with Cancer Chemotherapy," pp. 435–436, Oct. 2003.
Powis, G., International Encyclopedia of Pharmacology and Therapeutics, Anticancer Drugs: Antimetabolite Metabolism and Natural Anticancer Agents, pp 42–50, 1994.
Elasmar, et al., Jpn J Clin Oncol 2001; 31(4)172–174. Case Report: Hand–Foot Syndrome Induced by Oral Fluoropyrimidine S–1.
Ehrlanger M. et al., Dermatologica 140, Suppl. I. "Cutaneous Absorption and Urinary Excretion of 6–14C–5–Fluorouracil Ointment Applicated in an Ointment to Healthy and Diseased Human Skin," pp. 129–136, 1970.
Fischel J–L., et al., Proceedings of the American Association for Cancer Research, vol. 45. "Experimental arguments for a better understanding of hand–foot syndrome under capecitabine," p. 487, Mar. 2004.
Findlay M. et al., Annals of Oncology 7:47–53. "Measurement of plasma 5–fluorouracil by high–performance liquid chromatography with comparison of results to tissue drug levels observed using in vivo 19F magnetic resonance spectroscopy in patients in protracted venous infusion with or without interferon–α," pp. 111–117, 1996.
Fujii S. et al., Gann, 70. "Effect of Coadministration of Uracil or Cytosine on the Anti–Tumor Activity of Clinical Doses of 1–(2–Tetrahydrofuryl)–5–Fluorouracil and Level of 5–Fluorouracil in Rodents," pp. 209–214, Apr., 1979.
Fukushima S, et al., Cancer Research 52. "Carcinogenicity of Uracil, a Nongenotoxic Chemical, in Rats and Mice and Rationale," pp. 188–193, Apr. 1, 1992.
Gallo R, et al., The Journal of Clinical Investigation, vol. 48, "The Enzymatic Mechanisms for Deoxythymidine Synthesis in Human Leukocites," pp. 82–93, 1969.
Hatfield D., et al., The Journal of Biological Chemistry. "Synthesis of (3–Ribosyluric Acid) 5'–Phosphate and (3–Ribosylxanthine) 5'–Phosphate by a Pyrimidine Ribonucleotide Pyrophosphorylase of Beef Erythrocytes," pp. 60–66, Aug. 1964.
Paulo Hoff, Investigational New Drugs 18. "The tegafur–based dihydropyrimidine dehydrogenase inhibitory fluoropyrimidines, UFT/leucovorin (ORZEL™) and S–1: a review of their clinical development and therapeutic potential," pp. 153–163, 2000.
Ichikawa W., et al., British Journal of Cancer (2003) 89. "Both gene expression for orotate phosphoribosyltransferase and its ratio to dihydropyrimidine dehydrogenase influence outcome following fluoropyrimidine–based chemotherapy for metastatic colorectal cancer," 2003 Cancer Research UK.
Ikenaka K., et al., Gann, 70. "Effect of Uracil on Metabolism of 5–Fluorouracil in Vitro," pp. 353–359, Jun., 1979.
Johnson M., et al., Clinical Cancer Research, vol. 5. "Life–Threatening Toxicity in a Dihydropyrimidine Dehydrogenase–Deficient Patient after Treatment with Topical 5–Fluorouracil," pp. 141–146, Aug. 1999.
Kawaguchi Y., et al., Gann, 71. "Studies on the Metabolism of 1–(2–Tetrahydrofury)–5–Fluorouracil and Uracil Co–Adminstered Orally to Tumor–Bearing Rats," pp. 889–899, Dec., 1980.

(Continued)

Primary Examiner—Dwayne Jones
(74) Attorney, Agent, or Firm—Dechert LLP; Daniel M. Becker

(57) ABSTRACT

A method and composition is provided for organ rescue wherein a specific counter-measure is applied locally to a tissue at risk for or exhibiting an adverse side effect of a cancer treatment. More particularly, the method and composition is directed at controlling Hand-Foot Syndrome, a painful redness and cracking of the skin of the hands and feet which can occur with systemic treatment with 5-fluorouracil or a precursor thereof. Uracil ointment is applied to the skin of the hands and feet to prevent Hand-Foot Syndrome which can occur from systemic administration of 5-fluorouracil (or precursor thereof) as cancer treatment.

64 Claims, No Drawings

OTHER PUBLICATIONS

Largillier R., et al., General Poster Session. "Prospective Analysis of Dihydropyrimidine Dehydrogenase (Dpd) Activity for Predicting Capecitabin–Related Toxicities in Metastatic Breast Cancer Patients," p. 39, Mon, 9:00 AM—1:00 PM, 2002.

Leo S., et al., Journal of Chemotherapy, vol. 6, n. 6 "Dermatological Toxicity from Chemotherapy Containing 5–Fluorouracil," pp. 2–5, 1994.

Levy S., et al. Clinical Therapeutics/vol. 23, No. 6, "A Pharmacokinetic Evaluation of 0.5% and 5% Fluorouracil Topical Cream in Patients with Actinic Keratosis," pp. 908–920, 2001.

Luccioni, et al., Int. J. Cancer: 58, "Pyrimidine Nucleotide Metabolism in HUman Colon Carcinomas: Comparison of Normal Tissues Primary Tumors and Xenografts," pp. 32–37, 1994.

Mackean M., et al., Journal of Clinical Oncology, vol. 16, No. 9, "Phase I and Pharmacologic Study of Intermittent Twice–Daily Oral Therapy with Capecitabine in Patients with Advanced and/or Metastatic Cancer," pp. 2977–2985, Sep., 1998.

Machara Y., et al., Oncology, vol. 11, No. 9, "Scientific Basis for the Combination of Tegafur with Uracil," pp. 14–21, Supplement No. 10, 2001.

Malet–Martino M., et al., The Oncologist 2002, "Clinical Studies of Three Oral Prodrugs of 5–Fluorouracil (Capecitabine, UFT, S–1): A Review," pp. 288–323.

Niedzwicki J., et al., Biochemical Pharmacology, vol. 32, No. 3, "Structure–Activity Relationship of LIgands of the Pyrimidine Nucleoside Phosphorylases," pp. 399–415, 1983.

Niedzwicki J., et al., Biochemical Pharmacology, vol. 33, No. 15, "Structure–Activity Relationship of Pyrimidine Base Analogs as Ligands of Orotate Phosphoribosyltransferase," pp. 2383–2395, 1984.

Naguib, et al., Cancer Research 45, "Enzymes of Uracil Catabolism in Normal and Neoplastic Human Tissues," pp. 5405–5412, Nov. 1985.

Spicer E., et al., "Toxicity Study of Uracil in Dogs," pp. 199–204, 2003.

Senff H., et al., British Journal of Dermatology 118, "Topical 5–Fulorouracil Solution in the Treatment of Warts—Clinical Experience and Percutaneous Absorption," pp. 409–414, 1988.

Sawada N., et al., Clinical Cancer Research, vol. 4, "Induction of Thymidine Phosphorylase Activity and Enhancement of Capecitabine Efficacy by Taxol/Taxotere in Human Cancer Xenografts," pp. 1013–1019, Apr. 1998.

Sludden J., et al., Pharmacology, "Liver Dihydropyrimidine Dehydrogenase Activity in Human, Cynomolgus Monkey, Rhesus Monkey, Dog, Rat and Mouse," pp. 276–280, 1998.

Wang J., et al., Anticancer Research 24, "Oral 5–FU is a More Effective Antimetastatic Agent than UFT," pp. 1353–1360 (2004).

Ichikawa W., et al., Gastrointestinal Cancer, "Polymorphisms of orotate phosphoribosyl transferase (OPRT) gene and thymidylate synthase tandem repeat (TSTR) predict adverse events (AE) in colorectal cancer (CRC) patients treated with 5–fluorouracil (FU) pluis leucovorin (LV)," p. 1063, 2003.

Schilsky R.L., et al., Food and Drug Administration Center for Drug Evaluation and Reseach, "Sixty–Third Meeting of the Oncologic Drug Advisory Committee", Sep. 16, 1999.

Unknown, Oncology News International, "Lower Dose Capecitabine Is Active and Has Favorable Safety Profile in Elderly Patients With Advanced Breast Cancer," p. 40, Aug. 2003.

Unknown, Roche Pharmaceuticals, "Xeloda (capecitabine) Tablets," Apr. 2003.

Samid, D., Roche Laboratories Inc., "Important Information About Xeloda (capecitabine) Tablets," Aug. 2003.

Hartmann, H.R., et al., Med. Oncol. & Tumor Pharmacother. vol. 3 Nov. 2, "Modulation of the Effects of Fluoropyrimidines on Toxicity and Tumor Inhibition in Rodents by Uridine and Thymidine," pp. 111–118, Apr. 25, 1986.

Hejna, M. et al., "Decrease of duration and symptoms in chemotherapy–induced oral mucositis by topical GM–CSF: results of a prospective randomised trial", European Journal of Cancer 37(16), pp. 1994–2002, Nov. 2001.

Goodman & Gilman's The Pharmacological Basis of Therapeutics, $9^{th}$ Edition, 1996, pp. 1225–1229.

Stein, J.H., Editor–in–Chief, Internal Medicine, 4th Edition, Chapters 71 and 72 (pp. 699–715 only), 1994.

* cited by examiner

TREATMENT METHOD AGAINST SIDE-EFFECTS OF CHEMOTHERAPY

CROSS-REFERENCES

This application is a continuation-in-part application of Ser. No. 10/364,383 filed Feb. 12, 2003, now abandoned and which claims benefit from Provisional Application Ser. No. 60/355,764, filed Feb. 12, 2002.

BACKGROUND OF THE INVENTION

1. Field of the Invention

The invention concerns reducing side-effects of certain chemotherapy, and particularly, side-effects manifested topically in areas of the hands and feet.

2. The Related Art

Chemotherapy can result in predictable toxicity to organs. An important chemotherapy is the use of 5-fluorouracil (5 FU), and its precursors, such as capecitabine available as Xeloda®, a drug produced by Roche Pharmaceuticals. Xeloda® and 5 FU can induce a skin side effect called "Hand-Foot Syndrome" (HFS). This syndrome can cause pain, a loss of feeling (numbness), a tingling feeling, swelling and redness in the palms of your hands and/or soles of feet. Some patients also get a rash, discolored skin, nail problems, and hair loss. Severe cases of HFS can be very painful, cause skin of the hands and feet to blister and peel.

Compilations relevant to this field include the following.

Mackean M, Planting A, Twelves C et al: Phase 1 and pharmacologic study of intermittent twice-daily oral therapy with capecitabine in patients with advanced and/or metastatic cancer. J. Clin Oncol 16:2977–2985, 1998.

Cao S, Frank C, Shirasaka et al: 5-fluorouracil pro drug: role of anabolic and catabolic pathway modulation in therapy of colorectal cancer. Clin Can Res 1:839–845, 1995.

Hoff, P: The tegafur-based dehydropyrimidine dehydrogenase inhibitory fluoropyrimidines, UFT/Leucoverin (Orzel) and S-1: a review of their clinical development and therapeutic potential. Invest New Drugs 18:331–342, 2000.

Johnson M, Hageboutros A, Wang K, et al: Life threatening toxicity in a dihydropyrimidine dehydrogenase-deficient patient after treatment with topical 5-fluorouracil. Clin Can Res 5:2006–2011, 1999.

SUMMARY OF THE INVENTION

The present invention introduces the concept of "organ rescue." By applying locally a uracil ointment, certain adverse side effects of 5FU and its precursors can be averted. Uracil and 5FU are anabolized by the same enzymes. Uracil and 5FU differ chemically only in the H (Uracil) or F(5FU) at 5 position. Uracil is in high concentration when the uracil ointment is applied at the skin subject to HFS ("rescuing" the skin). After topical application of the uracil ointment to the hands and feet, uracil has negligible concentration in the body generally and specifically in the tumor containing regions of the body. The application of 1% uracil ointment prevents the anabolism of 5FU into a toxic form in those tissues, subjacent to the ointment application, where uracil concentration is high. Adverse side effects of 5FU are countered while preserving the anti-cancer systemic efficacy of the 5FU. With application of the uracil ointment to the hands and feet, the systemic uracil concentration is low. No longer is it necessary to reduce the systemic dose of 5FU/precursor in efforts to avoid the HFS side-effect.

The concept of "organ rescue" can be applied to other organs and to other chemotherapy agents which have specific organ toxicities. In each case, the rescue agent is directly applied in high local concentration to a tissue subject to toxicity thereby reversing the unwanted side effect of systematically administered anti-cancer agent. The rescue agent must, in each case, specifically reverse the local efficacy of the cancer treatment. The rescue agent must have negligible systemic concentration in the body to preserve the anti-cancer efficacy of the cancer treatment.

Previous work presumed the oral administration of uracil, systemically together with a precursor of 5FU would increase the metabolism of the 5FU and decrease its degradation. The resultant effect was presumed to be an increase in toxicity. This oral agent (UFT) is administered systematically at a dose of 1000–2000 mg uracil (4× molar excess over 5FU) per day. It is possible that the high uracil dose in UFT can counteract the anti-cancer effect of the 5FU. The 1% uracil ointment is administered at 1–2 cc or 10–20 mg uracil per day.

This logic for creating mixtures of uracil and 5FU/precursor was that the uracil compared to 5FU would be preferentially degraded and metabolized. Thus, the application of a 1% uracil ointment might be expected to increase HFS. Yet, quite the opposite was observed. The 1% uracil ointment eliminated the HFS toxicity of cancer treatment by 5FU or its precursor.

DETAILED DESCRIPTION OF THE INVENTION

Use of uracil formulations can be effective as post-chemotherapy treatment providing benefit to the adverse skin effects of the chemotherapy chemicals. Among those effects that can be mitigated include redness (erythema) and cracking.

Chemotherapy agents applicable to the present treatment and method include 5-fluorouracil or precursors thereof.

Amounts of uracil as the rescue active in rescue formulations may range from about 0.01 to about 60%, preferably from about 0.5 to about 5%, optimally from about 1% by weight.

Formulations of uracil may be in any convenient format. These include creams, lotions, aerosol sprays, roll-on liquids, sticks and pad forms.

Treatment compositions of the present invention may be anhydrous or emulsions. Oil and water emulsions are preferred for the present invention. Whether anhydrous or emulsion type, compositions of the present invention may further include a variety of pharmaceutically acceptable carriers and skin actives. Amounts of the carrier may range from about 1 to about 99%, preferably from about 5 to about 70%, optimally from about 10 to about 40% by weight. Among the carriers are emollients, water, inorganic powders, foaming agents, emulsifiers, fatty alcohols, fatty acids, and combinations thereof.

Emollients are substances selected from polyols, esters and hydrocarbons. Polyols suitable for the invention may include propylene glycol, dipropylene glycol, polypropylene glycol, polyethylene glycol, sorbitol, hydroxypropyl sorbitol, hexylene glycol, 1,3-butylene glycol, 1,2.6-hexanetriol, glycerin, ethoxylated glycerin, propoxylated glycerin, xylitol and mixtures thereof

Esters Useful as Emollients Include (1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are C12–C15 alcohol benzoate esters.

(2) Alkenyl esters of fatty acids having 10 to 20 carbon atoms. Examples thereof include oleyl myristate, oleyl stearate and oleyl oleate.

(3) Ether-esters such as fatty acids esters of ethoxylated fatty alcohols.

(4) Polyhydric alcohol esters. Ethylene glycol mono and di-fatty acid esters, diethylene glycol mono- and di-fatty acid esters, polyethylene glycol (200–6000) mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterol esters, of which cholesterol fatty acid esters are examples thereof.

Illustrative hydrocarbons are mineral oil, polyalphaolefins, petrolatum, isoparaffin, polybutenes and mixtures thereof.

Inorganic powders are useful carriers. Examples include clays (such as Montmorillonite, Hectorite, Laponite and Bentonite), talc, mica, silica, alumina, zeolites, sodium sulfate, sodium bicarbonate, sodium carbonate, calcium sulfate and mixtures thereof.

Aerosol propellants may also be used as carriers. Propellants are normally based on volatile hydrocarbons such as propane, butane, isobutene, pentane, isopropane and mixtures thereof Philipps Petroleum Company is a source of such propellants under trademarks including A31, A32, A51 and A70. Halocarbons including fluorocarbons and dimethyl ether are further widely employed propellants.

Emulsifiers may constitute at least a portion of the carrier for compositions according to the present invention. These may be selected from nonionic, anionic, cationic, or amphoteric emulsifying agents. They may range in amount anywhere from about 0.1 to about 20% by weight. Illustrative nonionic emulsifiers are alkoxylated compounds based on C10–C22 fatty alcohols and acids and sorbitan. These materials are available, for instance, from the Shell Chemical Company under the Neodol trademark. Copolymers of polyoxypropylenepolyoxyethylene sold by the BASF Corporation under the Pluronic trademark are sometimes also useful. Alkyl polyglycosides available from the Henkel Corporation may also be utilized for purposes of this invention.

Anionic type emulsifiers include fatty acid soaps, sodium lauryl sulphate, sodium lauryl ether sulphate, alkyl benzene sulphonate, mono- and di-alkyl acid phosphates, sarcosinates, taurates and sodium fatty acyl isethionate.

Amphoteric emulsifiers include such materials as dialkylamine oxide and various types of betaines (such as cocamidopropyl betaine).

Preservatives such as methyl paraben and propyl paraben are useful to prevent microbial contamination.

Another system for delivering uracil and similar rescue agents may be microsphere technology. Typical of this technology is use of a high surface area polymethacrylate impregnated with the rescue agent.

Except in the operating and comparative examples, or where otherwise explicitly indicated, all numbers in this description indicating amounts of material ought to be understood as modified by the word "about."

The following examples will more fully illustrate the embodiments of this invention. All parts, percentages and proportions referred to herein and in the appended claims are by weight unless otherwise illustrated.

All documents mentioned in this application should be considered as being incorporated herein by reference.

EXAMPLE 1

A patient being treated with orally administered Xeloda had to discontinue the routine after only 5 of 14 days of planned treatment. Discontinuance was the result of severe Hand-Foot Syndrome. Tumor measurements on the original date and after 21 days subsequent to Hand-Foot Syndrome recovery are recorded in Table 1 below as "initial" and "Day 21," respectively. After two courses of treatment with Xeloda® and a concurrent topical application of 1% uracil ointment based on a vanishing cream base (applied four times a day to the hands and feet), the patient had no symptoms of the syndrome. See "Day 35."

TABLE 1

| Tumor | Original Date | Day 21 | Day 35 |
| --- | --- | --- | --- |
| Breast mass | 7 × 7 cm | 9 × 9 cm | 8.5 × 8.5 cm |
| Left supraclavicular node | 1 × 1 cm | 2 × 2 cm | 1.5 × 1.5 cm |
| Right axillary mass | 2 × 2 cm | 3 × 3 cm | 2 × 2 cm |

The administration of the uracil ointment both prevented the Hand-Foot Syndrome as well as restored the anti-tumor activity of the Xeloda®.

This 48 year old female patient exhibited metastatic breast cancer. She had refused mastectomy and had previously failed adriamycin and cytoxan, weekly taxol, weekly navelbine. She was then placed on Xeloda® together with 1% uracil ointment applied to the hands and feet. The 1% uracil ointment was used starting with cycle 5 of treatment with Xeloda®. Table 2 below summarizes results on this patient.

TABLE 2

| Course q3 wk | 1 | 2 | 3 | 4 | 5 | 6 | 7 | 8 |
| --- | --- | --- | --- | --- | --- | --- | --- | --- |
| Xeloda dose 14/21 days | 1250 mg/m2 bid × 14 | same | D/C after 4 days | 1000 mg/m2 bid × 14 | 1250 mg/m2 bid × 14 | same | same | same |
| Taxotere 75 mg/m2 | + | + | + | + | + | + | + | + |
| Marker tumor size cm-prior to rx | 12 × 12 | 8 × 8 | 7 × 7 | 7 × 7 | 9 × 9 progression on lower dose Xeloda | 8.5 × 8.5 | 8 × 8 | 8.5 × 8.5 |

TABLE 2-continued

| Course q3 wk | 1 | 2 | 3 | 4 | 5 | 6 | 7 | 8 |
|---|---|---|---|---|---|---|---|---|
| 1% uracil ointment | 0 | 0 | 0 | 0 | + | + | + | + |
| Hand-foot syndrome | ND* | ND | ++++ | ++ | 0 | 0 | 0 | 0 |

*Not described

The 1% uracil ointment allowed a reescalation of the dose of Xeloda®. The results show recovered anti-tumor activity at the higher dose of Xeloda®. The 1% uracil ointment did not interfere with the anti-cancer activity of the Xeloda®. Neither did the 1% uracil ointment have any discernible toxicity.

EXAMPLE 2

Another patient, a 68 year old white female diagnosed with metastatic colon cancer, was treated with Xeloda® and thalidomide. Hand-Foot Syndrome developed. Complete reversal of the syndrome occurred after topical treatment with a 1% uracil ointment. The efficacy of the Xeloda® and thalidomide treatment was unaffected by the concurrent use if the 1% uracil ointment. There were no dose reductions of chemotherapy or treatment delays.

EXAMPLE 3

A 60 year old white female with metastatic colon cancer was treated with 5FU, Leucovocin®, and Oxaliplatin, a very common regime of treatment for this form of cancer. The patient developed hand-foot syndrome. Topical application of 1% uracil ointment resulted in complete resolution of the syndrome. The anti-cancer treatment remained efficacious. No side-effects were noted as a result of the uracil ointment applications. There were no dose reductions of chemotherapy or treatment delays.

The foregoing description and examples illustrate selected embodiments of the present invention. In light thereof, variations and modifications will be suggested to one skilled in the art, all of which are within the spirit and purview of this invention.

What is claimed is:

1. A method of reducing cutaneous side-effects of systemic therapy with 5-fluorouracil (5-FU) or a precursor of 5-FU, the method comprising:
applying uracil topically to the skin of a patient being treated concurrently and systemically with 5-fluorouracil (5-FIT) or a precursor of 5-FU in an amount effective to reduce, at the site of topical uracil administration, the development of cutaneous side-effects.

2. The method of claim 1, wherein the systemic therapeutic is a 5-fluorouracil precursor.

3. The method of claim 2, wherein said precursor is capecitabine.

4. The method of claim 1, wherein uracil is applied in a composition that further comprises a pharmaceutically acceptable carrier.

5. The method of claim 4, wherein uracil is present within said composition at a concentration by weight of at least about 0.1%.

6. The method of claim 5, wherein uracil is present within said composition at a concentration by weight of at least about 1%.

7. The method of claim 4, wherein uracil is present within said composition at a concentration by weight of no more than about 60%.

8. The method of claim 7, wherein uracil is present within said composition at a concentration by weight of no more than about 5%.

9. The method of claim 4, wherein uracil is present within said composition at a concentration by weight of about 1%.

10. The method of claim 4, wherein said composition is either anhydrous or an emulsion.

11. The method of claim 10, wherein said composition is an emulsion.

12. The method of claim 4, wherein said composition is selected from the group consisting of creams, lotions, ointments, aerosol sprays, roll-on liquids, roll-on sticks and pads.

13. The method of claim 4, wherein said carrier comprises at least one agent selected from the group consisting of emollients, water, inorganic powders, foaming agents, emulsifiers, fatty alcohols, fatty acids, and combinations thereof.

14. The method of claim 13, wherein said carrier comprises at least one emollient.

15. The method of claim 14, wherein said at least one emollient is selected from the group consisting of polyols, esters, and hydrocarbons.

16. The method of claim 15, wherein said polyol is selected from the group consisting of propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin, xylitol, and mixtures thereof.

17. The method of claim 15, wherein said ester is selected from the group consisting of alkyl esters of fatty acids having 10 to 20 carbon atoms.

18. The method of claim 15, wherein said ester is selected from the group consisting of hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate and cetyl lactate.

19. The method of claim 15, wherein said ester is a C12–C15 alcohol benzoate ester.

20. The method of claim 19, wherein said ester is oleyl myristate, oleyl stearate or oleyl oleate.

21. The method of claim 15, wherein said ester is a fatty acid ester of an ethoxylated fatty alcohol.

22. The method of claim 15, wherein said ester is a polyhydric alcohol ester.

23. The method of claim 22, wherein said ester is selected from the group consisting of ethylene glycol mono- and di-fatty acid esters, diethylene glycol mono- and di-fatty acid esters, polyethylene glycol (200–6000) mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

24. The method of claim 15, wherein said ester is a wax ester.

25. The method of claim 24, wherein said wax ester is selected from the group consisting of beeswax, spermaceti, myristyl myristate and stearyl stearate.

26. The method of claim 15, wherein said ester is a sterol ester.

27. The method of claim 13, wherein said carrier comprises an inorganic powder.

28. The method of claim 27, wherein said inorganic powder is selected from the group consisting of clays, talc, mica, silica, alumina, zeolites, sodium sulfate, sodium bicarbonate, sodium carbonate, calcium sulfate and mixtures thereof.

29. The method of claim 4, wherein said carrier comprises an aerosol propellant.

30. The method of claim 29, wherein said propellant is selected from the group consisting of propane, butane, isobutene, pentane, isopropane, fluorocarbons, dimethylether and mixtures thereof.

31. The method of any one of claims 1 or 2, wherein uracil is applied topically to the skin of the foot, the hand, or both the foot and hand.

32. A method of treating breast or colorectal cancer with reduced cutaneous side-effects, the method comprising:

systemically administering 5-fluorouracil (5-FU) or a precursor of 5-FU to a patient having breast or colorectal cancer; and concurrently applying uracil topically to the patient's skin in an amount effective to reduce, at the site of topical uracil administration, the development of cutaneous side-effects.

33. The method of claim 32, wherein the systemically administered therapeutic is a 5-fluorouracil precursor.

34. The method of claim 33, wherein said precursor is capecitabine.

35. The method of claim 32, wherein uracil is applied in a composition that further comprises a pharmaceutically acceptable carrier.

36. The method of claim 35, wherein uracil is present within said composition at a concentration by weight of at least about 0.1%.

37. The method of claim 36, wherein uracil is present within said composition at a concentration by weight of at least about 1%.

38. The method of claim 35, wherein uracil is present within said composition at a concentration by weight of no more than about 60%.

39. The method of claim 38, wherein uracil is present within said composition at a concentration by weight of no more than about 5%.

40. The method of claim 35, wherein uracil is present within said composition at a concentration by weight of about 1%.

41. The method of claim 35, wherein said composition is either anhydrous or an emulsion.

42. The method of claim 41, wherein said composition is an emulsion.

43. The method of claim 35, wherein said composition is selected from the group consisting of creams, lotions, ointments, aerosol sprays, roll-on liquids, roll-on sticks and pads.

44. The method of claim 35, wherein said carrier comprises at least one agent selected from the group consisting of emollients, water, inorganic powders, foaming agents, emulsifiers, fatty alcohols; fatty acids, and combinations thereof.

45. The method of claim 44, wherein said carrier comprises at least one emollient.

46. The method of claim 45, wherein said at least one emollient is selected from the group consisting of polyols, esters, and hydrocarbons.

47. The method of claim 46, wherein said polyol is selected from the group consisting of propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin, xylitol, and mixtures thereof.

48. The method of claim 46, wherein said ester is selected from the group consisting of alkyl esters of fatty acids having 10 to 20 carbon atoms.

49. The method of claim 46, wherein said ester is selected from the group consisting of hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate and cetyl lactate.

50. The method of claim 46, wherein said ester is a C12–C15 alcohol benzoate ester.

51. The method of claim 50, wherein said ester is oleyl myristate, oleyl stearate or oleyl oleate.

52. The method of claim 46, wherein said ester is a fatty acid ester of an ethoxylated fatty alcohol.

53. The method of claim 46, wherein said ester is a polyhydric alcohol ester.

54. The method of claim 53, wherein said ester is selected from the group consisting of ethylene glycol mono- and di-fatty acid esters, diethylene glycol mono- and di-fatty acid esters, polyethylene glycol (200–6000) mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

55. The method of claim 46, wherein said ester is a wax ester.

56. The method of claim 55, wherein said wax ester is selected from the group consisting of beeswax, spermaceti, myristyl myristate and stearyl stearate.

57. The method of claim 46, wherein said ester is a sterol ester.

58. The method of claim 44, wherein said carrier comprises an inorganic powder.

59. The method of claim 58, wherein said inorganic powder is selected from the group consisting of clays, talc, mica, silica, alumina, zeolites, sodium sulfate, sodium bicarbonate, sodium carbonate, calcium sulfate and mixtures thereof.

60. The method of claim 35, wherein said carrier comprises an aerosol propellant.

61. The method of claim 60, wherein said propellant is selected from the group consisting of propane, butane, isobutene, pentane, isopropane, fluorocarbons, dimethylether and mixtures thereof.

62. The method of any one of claims 32–61, wherein uracil is applied topically to the skin of the foot, the hand, or both the foot and hand.

63. The method of any one of claims 32–61, wherein the cancer is breast cancer.

64. The method of any one of claims 32–61, wherein the cancer is colorectal cancer.

* * * * *

UNITED STATES PATENT AND TRADEMARK OFFICE
CERTIFICATE OF CORRECTION

PATENT NO.   : 6,979,688 B2
DATED        : December 27, 2005
INVENTOR(S)  : John P. Ford It is certified that error appears in the above-identified patent and that said Letters Patent is hereby corrected as shown below:

Column 5,
Line 46, "(5-FIT)" should read -- (5-FU) --.

Column 6,
Line 14, "any one of claims 1 or 2" should read -- any one of claims 1-30 --.

Signed and Sealed this

Twenty-first Day of February, 2006

JON W. DUDAS
*Director of the United States Patent and Trademark Office*